(12) United States Patent
Wong et al.

(10) Patent No.: US 10,988,638 B2
(45) Date of Patent: Apr. 27, 2021

(54) PROCESS TO REDUCE ENDOTOXIN IN GELATIN

(71) Applicant: Catalent U.K. Swindon Zydis Limited, Swindon (GB)

(72) Inventors: Yik Teng Wong, Royal Wotton Bassett (GB); Khojasteh Shirkhani, Swindon (GB); Ami Powe, Swindon (GB); Sarah Stewart, Burbage (GB); Charli Smardon, Chippenham (GB)

(73) Assignee: Catalent U.K. Swindon Zydis Limited, Swindon (GB)

( * ) Notice: Subject to any disclaimer, the term of this patent is extended or adjusted under 35 U.S.C. 154(b) by 0 days.

(21) Appl. No.: 16/295,223

(22) Filed: Mar. 7, 2019

(65) Prior Publication Data

US 2019/0276707 A1   Sep. 12, 2019

Related U.S. Application Data

(60) Provisional application No. 62/640,394, filed on Mar. 8, 2018.

(51) Int. Cl.
| | |
|---|---|
| *C09H 3/02* | (2006.01) |
| *A61K 9/51* | (2006.01) |
| *A61K 9/00* | (2006.01) |
| *B01J 41/12* | (2017.01) |
| *B01J 47/014* | (2017.01) |
| *B01J 47/12* | (2017.01) |
| *A61K 9/19* | (2006.01) |
| *A61K 47/42* | (2017.01) |

(52) U.S. Cl.
CPC .............. *C09H 3/02* (2013.01); *A61K 9/006* (2013.01); *A61K 9/0019* (2013.01); *A61K 9/19* (2013.01); *A61K 9/5169* (2013.01); *A61K 47/42* (2013.01); *B01J 41/12* (2013.01); *B01J 47/014* (2017.01); *B01J 47/12* (2013.01)

(58) Field of Classification Search
None
See application file for complete search history.

(56) References Cited

U.S. PATENT DOCUMENTS

| | | | |
|---|---|---|---|
| 4,305,502 A | 12/1981 | Gregory et al. | |
| 4,371,516 A | 2/1983 | Gregory et al. | |
| 4,374,063 A | 2/1983 | Consolazio et al. | |
| 4,758,598 A | 7/1988 | Gregory | |
| 6,709,669 B1 | 3/2004 | Murray et al. | |
| 2003/0064074 A1* | 4/2003 | Chang | A61K 8/65 |
| | | | 424/184.1 |

FOREIGN PATENT DOCUMENTS

| | | |
|---|---|---|
| EP | 1829946 | 9/2007 |
| GB | 211423 | 2/1924 |
| GB | 1548022 | 7/1979 |
| JP | 2007-211170 | 8/2007 |
| WO | 2011/115969 A2 | 9/2011 |

OTHER PUBLICATIONS

Hirayama et al. 2002 (Chromatographic removal of endotoxin from protein solutions by polymer particles; Journal of Chromatography B 781:419-432) (Year: 2002).*
International Search Report and Written Opinion dated Aug. 13, 2019, directed to International Application No. PCT/IB2019/000234; 12 pages.

* cited by examiner

*Primary Examiner* — Mary Maille Lyons
(74) *Attorney, Agent, or Firm* — Morrison & Foerster LLP

(57) ABSTRACT

The present disclosure is directed to processes for reducing the endotoxin level in gelatin and the resulting gelatin with low endotoxin content. The process includes dissolving a salt in a gelatin solution and filtering the gelatin-salt solution using anion exchange to reduce the endotoxin level. After reducing the endotoxin level of the gelatin-salt solution, the low endotoxin gelatin-salt solution is desalted to remove the salt, thereby producing a low endotoxin gelatin solution.

18 Claims, 9 Drawing Sheets

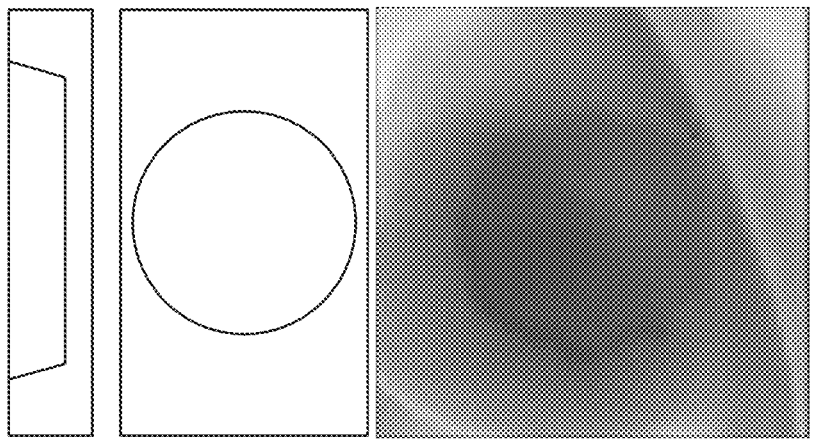
FIG. 9C SKIN REMAINS
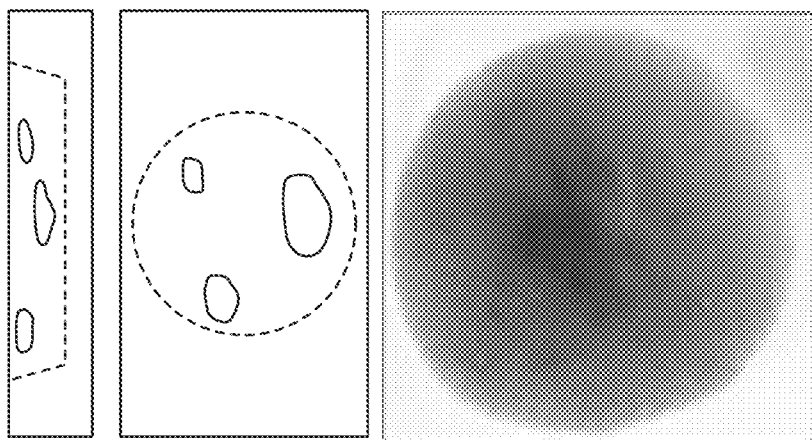
FIG. 9B LUMPS
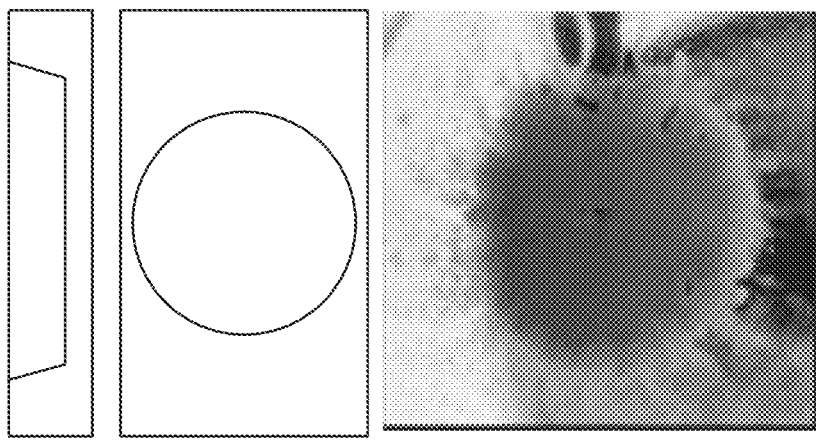
FIG. 9A FULLY WETTED

PROCESS TO REDUCE ENDOTOXIN IN GELATIN

REFERENCE TO RELATED APPLICATIONS

This application claims the benefit of U.S. Provisional Application No. 62/640,394, filed Mar. 8, 2018, the entire contents of which are incorporated herein by reference.

FIELD OF THE INVENTION

This disclosure relates to a process for reducing endotoxin in gelatin. More specifically, this disclosure relates to a process for reducing endotoxin in gelatin by filtering a gelatin-salt solution using anion exchange and desalting the filtered gelatin-salt solution.

BACKGROUND OF THE INVENTION

Vaccines are traditionally delivered by parenteral delivery via inter-muscular, inter-dermal, or subcutaneous routes. However, mucosal vaccine delivery (via the buccal, sublingual, nasal, oral, or vaginal mucosa) has received increasing interest as a means of inducing local and distant antibody immune response as well as systemic immune response. In addition, mucosal vaccine delivery by solid dosage forms (e.g., buccal/sublingual tablet, oral tablet or capsules, vaginal insert) offers several advantages such as the potential for mass immunization as well as cold-chain independent capability. Furthermore, mucosal vaccine delivery can be suitable for patients that have injection phobia and the patient can self-administrate the vaccine. The buccal/sublingual route has been used for many years to deliver drugs and small molecules to the bloodstream, but its application as a means of mucosal delivery for vaccines has received little attention.

One of the main considerations for mucosal vaccine delivery is the level of endotoxin present in the pharmaceutical composition. Endotoxin is a complex lipopolysaccharide ("LPS") found in the outer membrane of gram negative bacteria that is released after the death or lysis of the cell. Endotoxin can cause physiological changes in the human body and thus can impact organ systems and disrupt the humoral and cellular human mediation systems. For parenteral delivery products, there is a strict limit in the endotoxin content because the human body can only tolerate a small amount of endotoxin in the blood.

However, there is typically a small safety concern when ingesting buccal/sublingual products that contain high endotoxin levels because the mouth is colonized by aerobic and anaerobic bacteria. For example, a healthy adult with good oral hygiene has a mean level of endotoxins derived from the mouth microflora of about 2 endotoxin units (EU)/ml of saliva (1 ng=10 EU). Thus, the daily production of endotoxin is greater than 1000 EU/day for a healthy adult with good oral hygiene. However, in terms of vaccine delivery, endotoxin can eliminate, shut down, or amplify the immune response depending on the mucosa site.

SUMMARY OF THE INVENTION

The level of endotoxin in buccal/sublingual products used for vaccination (especially against infection) can either positively or negatively influence the immune response. In addition, for mucosal delivery, adjuvants are often added to improve the immune response. The presence of endotoxins can negatively or positively mask the benefit of a given adjuvant. Furthermore, endotoxin has been suggested to induce tolerance towards antigens at the sublingual level, which could counteract the adjuvant immunostimulatory role. Accordingly, dosage forms such as buccal/sublingual tablets (used for mucosal vaccine delivery to treat infection) should have low endotoxin content.

Many dosage forms use matrix formers to provide oral dispersible properties. Gelatin is one of the main matrix formers. Gelatin is derived from hydrolysis of collagen in acidic or alkaline conditions. As it is a natural-derived product, it contains variably high amounts of endotoxin. For example, in fish gelatin, the endotoxin level can range from 6000-30,000 EU/gram of gelatin. Other gelatins can have an endotoxin content of at least about 3,000 EU/g, about 4,000 EU/g, about 5,000 EU/g, about 6,000 EU/g, about 10,000 EU/g, about 12,000 EU/g, about 14,000 EU/g, about 15,000 EU/g, about 20,000 EU/g, about 25,000 EU/g, or about 30,000 EU/g.

Accordingly, to produce dosage forms made from gelatin having low endotoxin content, Applicants discovered a process that reduces the amount of endotoxin in gelatin. The resulting low endotoxin gelatin can then be used as a matrix former to create various dosage forms. In addition, the low endotoxin gelatin can be used in a variety of other areas such as stick pack granules and softgels.

Provided herein are processes for reducing the endotoxin level in gelatin and the resulting gelatin with low endotoxin content. The process includes dissolving a salt in a gelatin solution and filtering the gelatin-salt solution using anion exchange to reduce the endotoxin level. After reducing the endotoxin level of the gelatin-salt solution, the low endotoxin gelatin-salt solution is desalted, thereby producing a low endotoxin gelatin solution. The low endotoxin gelatin solution can be used in various pharmaceutical compositions including vaccines.

In some embodiments, a method for reducing endotoxin in gelatin includes dissolving a salt in a gelatin solution comprising gelatin and a solvent to form a gelatin-salt solution, wherein the endotoxin content of the gelatin is at least 6,000 EU/g; filtering the gelatin-salt solution through an anion exchange adsorber such that a filtrate gelatin-salt solution has an endotoxin content of less than 2,500 EU/g; desalting the filtrate gelatin-salt solution to form a low endotoxin gelatin solution that has an endotoxin content of less than 2,500 EU/g. In some embodiments, the salt concentration in the gelatin-salt solution is 75-300 mM. In some embodiments, the salt concentration of the gelatin-salt solution is about 145-155 mM. In some embodiments, the gelatin solution is a 1-20% w/w gelatin solution. In some embodiments, the salt is sodium chloride. In some embodiments, the gelatin is fish gelatin. In some embodiments, dissolving the salt in the gelatin solution comprises heating the gelatin solution to 50-70° C. In some embodiments, the solvent is water. In some embodiments, the endotoxin content of the gelatin-salt solution and the low endotoxin gelatin solution is less than 1,000 EU/g. In some embodiments, filtering the gelatin-salt solution through an anion exchange adsorber can reduce the endotoxin content of the solution by at least 95%. In some embodiments, at least about 85% of the gelatin content is recovered in the filtrate gelatin-salt solution after filtering the gelatin-salt solution through an anion exchange adsorber. In some embodiments, the method further includes removing the solvent from the low endotoxin gelatin solution to form a low endotoxin gelatin that has an endotoxin content of less than 2,500 EU/g.

In some embodiments, desalting the filtrate gelatin-salt solution is accomplished by a diafiltration process. In some embodiments, the diafiltration process comprises diluting the filtrate gelatin-salt solution with a second solvent and filtering the diluted filtrate gelatin-salt solution to form a diluted filtrate gelatin solution. In some embodiments, the diluted filtrate gelatin-salt solution is filtered until a conductivity of the diluted filtrate gelatin solution is within less than 25% of a conductivity of the gelatin solution. In some embodiments, the ratio of filtrate gelatin-salt solution to second solvent is 1:1-1:4. In some embodiments, the second solvent is removed from the diluted filtrate gelatin solution to form the low endotoxin gelatin solution. In some embodiments, the second solvent is removed from the diluted filtrate gelatin solution until a weight of the diluted filtrate gelatin solution is within less than 5% of a weight of the filtrate gelatin-salt solution. In some embodiments, the second solvent comprises water.

In some embodiments, a low endotoxin gelatin solution is prepared by a process that includes dissolving a salt in a gelatin solution comprising gelatin and a solvent to form a gelatin-salt solution, wherein the endotoxin content of the gelatin is at least 6,000 EU/g; filtering the gelatin-salt solution through an anion exchange adsorber such that a filtrate gelatin-salt solution has an endotoxin content of less than 2,500 EU/g; desalting the filtrate gelatin-salt solution to form a low endotoxin gelatin solution that has an endotoxin content of less than 2,500 EU/g. In some embodiments, a low endotoxin gelatin solution includes a solvent and a gelatin, wherein the gelatin has an endotoxin content of less than 2,500 EU/g.

In some embodiments, a method of producing a dosage form for the delivery of a pharmaceutically active ingredient includes dissolving a salt in a gelatin solution comprising gelatin and a solvent to form a gelatin-salt solution, wherein the endotoxin content of the gelatin is at least 6,000 EU/g; filtering the gelatin-salt solution through an anion exchange adsorber such that a filtrate gelatin-salt solution has an endotoxin content of less than 2,500 EU/g; desalting the filtrate gelatin-salt solution to form a low endotoxin gelatin solution that has an endotoxin content of less than 2,500 EU/g; dosing a formulation comprising the low endotoxin gelatin solution into a preformed mold; and freeze drying the low endotoxin gelatin solution to form the dosage form.

In some embodiments, a dosage form for the delivery of a pharmaceutically active ingredient is prepared by a process that includes dissolving a salt in a gelatin solution comprising gelatin and a solvent to form a gelatin-salt solution, wherein the endotoxin content of the gelatin is at least 6,000 EU/g; filtering the gelatin-salt solution through an anion exchange adsorber such that a filtrate gelatin-salt solution has an endotoxin content of less than 2,500 EU/g; desalting the filtrate gelatin-salt solution to form a low endotoxin gelatin solution that has an endotoxin content of less than 2,500 EU/g; dosing a formulation comprising the low endotoxin gelatin solution into a preformed mold; and freeze drying the low endotoxin gelatin solution to form the dosage form.

Additional advantages will be readily apparent to those skilled in the art from the following detailed description. The examples and descriptions herein are to be regarded as illustrative in nature and not restrictive.

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

BRIEF DESCRIPTION OF THE DRAWINGS

Exemplary embodiments are described with reference to the accompanying figures, in which:

FIG. 9A is a schematic representation with a picture of a fully wetted tablet.

FIG. 9B is a schematic representation with a picture of a tablet with hard lumps.

FIG. 9C is a schematic representation with a picture of a tablet with a film of collapsed formulation matrix that forms at the surface of the freeze dried tablet (skin).

In the Figures, like reference numbers correspond to like components unless otherwise stated. In addition, the Figures are not drawn to scale.

DETAILED DESCRIPTION OF THE INVENTION

Figure 1:
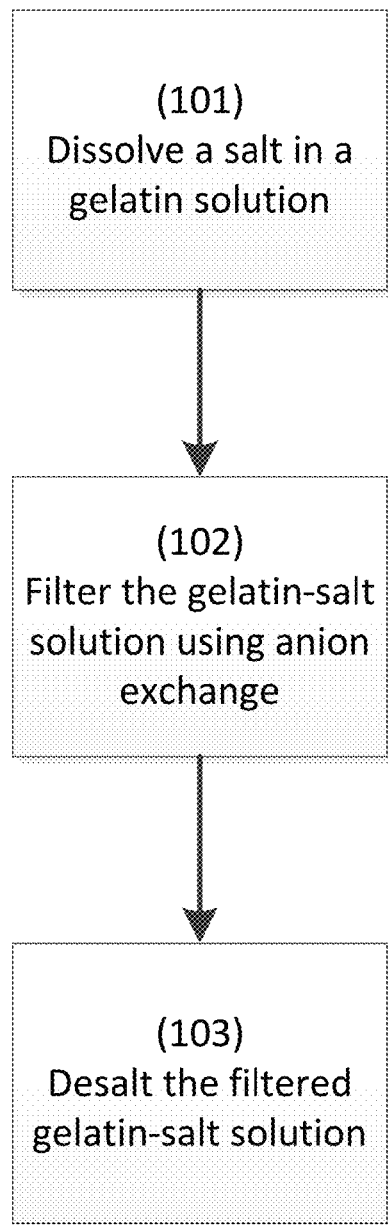
FIG. 1 illustrates a flowchart for a method of reducing endotoxin in gelatin disclosed herein.

The processes disclosed herein can create gelatin with low endotoxin levels. The low endotoxin gelatin can then be used for a variety of applications including, but not limited to, as a matrix former in a pharmaceutical dosage form. FIG. 1 illustrates a flowchart for method 100 of reducing endotoxin in gelatin.

Preparation of a Gelatin-Salt Solution

Figure 2:
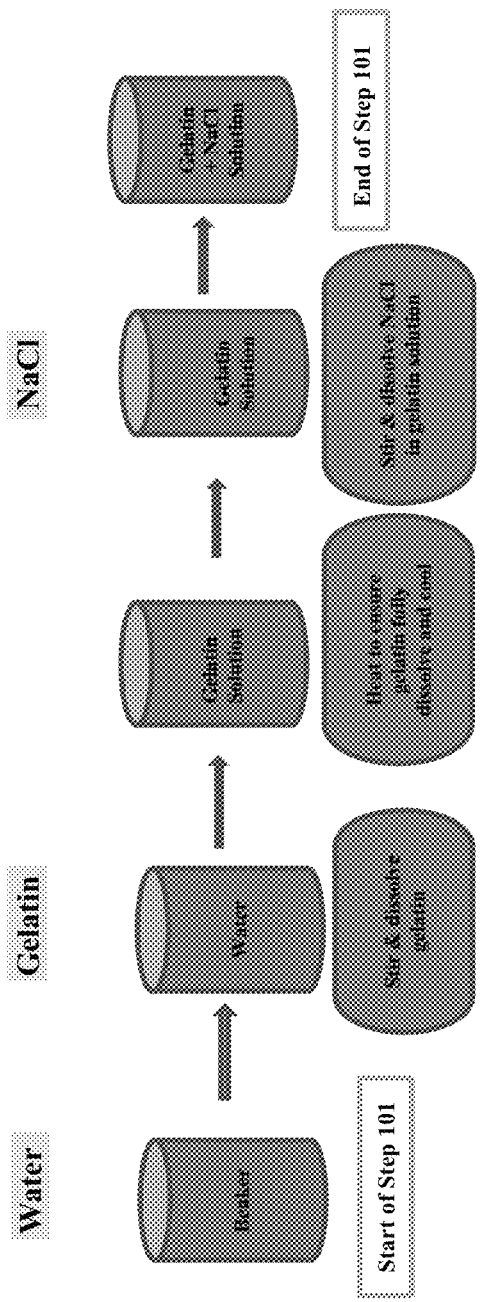
FIG. 2 illustrates a flowchart for a step of creating a gelatin-salt solution.

A first step 101 can involve preparing a gelatin-salt solution by dissolving salt into a gelatin solution. FIG. 2 illustrates a flowchart for step 101 of dissolving salt into a gelatin solution. The initial gelatin solution can have an endotoxin content equivalent to that of the gelatin in the solution. In addition, the gelatin-salt solution will also have an endotoxin content comparable to the initial gelatin solution.

Step 101 can include dissolving a gelatin in a solvent to form a gelatin solution. Preferably, the gelatin is fully dissolved in the solvent. Dissolving the gelatin in the solvent can be aided by stirring and/or heating the solution. In some embodiments, the gelatin solution can be heated to about 40-80° C., about 50-70° C., about 55-65° C., about 58-62° C., or about 60° C. to facilitate the gelatin's dissolving in the solvent. After the gelatin has fully dissolved in the solvent, the gelatin solution can be cooled to room temperature.

In some embodiments, the gelatin can be a non-gelling gelatin, a gelling gelatin including fish gelatin, bovine gelatin, porcine gelatin, chicken gelatin, or a combination thereof. Although the examples disclosed below use fish gelatin as a model gelatin, the principles established for the processes disclosed herein are applicable to other gelatin types and the respective gelatin grades available within each gelatin type. In some embodiments, the solvent can be water (including purified water).

The gelatin concentration in the gelatin solution can vary depending on the final use of the gelatin. As such, the specific amount of gelatin and the specific amount of solvent used can vary depending on the desired gelatin concentration. In some embodiments, the gelatin concentration in the gelatin solution can be about 1-20% w/w, about 2-15% w/w, about 3-12% w/w, about 5-12% w/w, about 8-12% w/w, or about 10-12% w/w.

Prior to adding the salt to the gelatin solution, the conductivity of the gelatin solution can be measured. Such a pre-salting conductivity measurement can be useful when comparing the final low endotoxin gelatin solution after the desalting process. In addition, the conductivity of the gelatin-salt solution can also be measured prior to the endotoxin reduction step.

As shown in FIG. 2, the gelatin can be fully dissolved in the solvent to form the gelatin solution. The dissolution of gelatin can be aided by stirring and heating the gelatin solution. Salt can be dissolved in the gelatin solution to form a gelatin-salt solution.

In some embodiments, the salt can be sodium chloride, potassium chloride, lithium chloride, calcium chloride, other chloride salts, or combinations thereof.

As described in more detail below, Applicants discovered that the concentration of the salt in the gelatin-salt solution plays a critical role in the anion exchange process in step 102 for removing endotoxin from the gelatin. Specifically, Applicants discovered that performing anion exchange without the use of a salt in the gelatin solution can cause the gelatin to block/clog the filters used during the anion exchange process in step 102.

Furthermore, as explained below in the description of step 102, Applicants discovered that the specific salt concentration has a direct impact on the endotoxin removal step. As such, the salt concentration in the gelatin-salt solution can be about 50-500 mM, about 75-300 mM, about 100-200 mM, about 125-175 mM, about 140-160 mM, about 145-155 mM, or about 150 mM.

Figure 3:
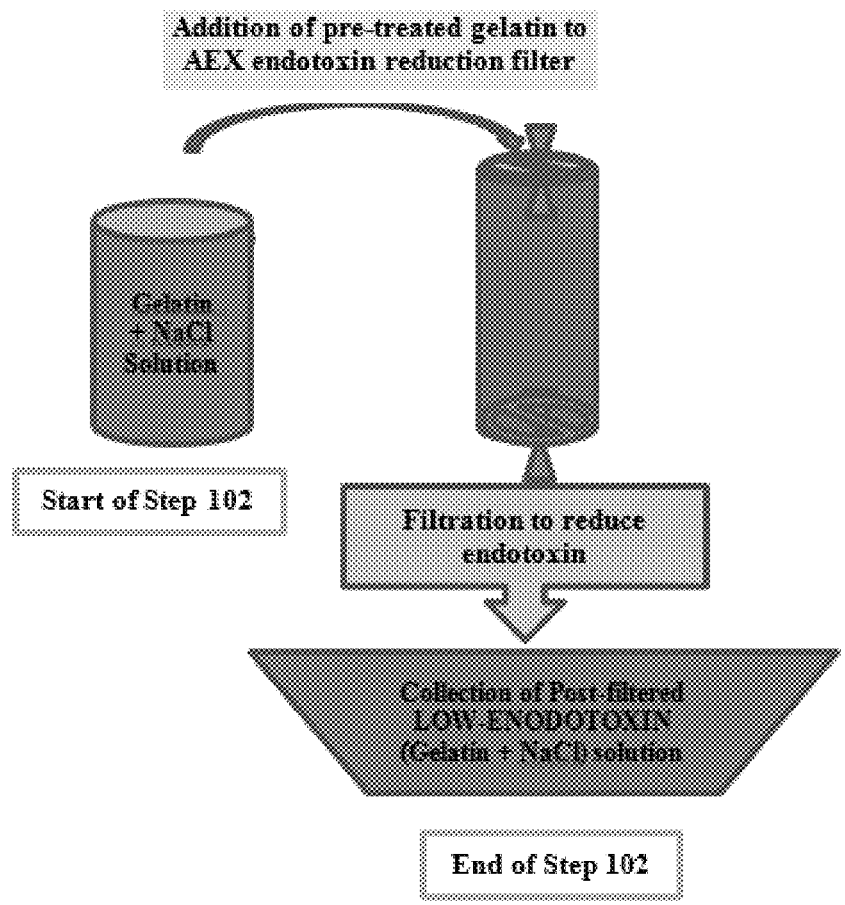
FIG. 3 illustrates a flowchart for a step of filtering a gelatin-salt solution using anion exchange to remove endotoxin disclosed herein.

Endotoxin Reduction by Filtration of the Gelatin-Salt Solution Using Anion Exchange After the preparation of the gelatin-salt solution, endotoxin can be removed from the gelatin in step 102. FIG. 3 illustrates a flowchart for step 102 of filtering the gelatin-salt solution using anion exchange ("AEX"). Applicants discovered that using the principles of Anion Exchange Chromatography, endotoxin can be removed from the gelatin solution. Anion Exchange Chromatography involves the separation of molecules on the basis of their charge. Specifically, anion exchange chromatography uses a positively charged ion exchange resin with an affinity for molecules having net negative surface charges. Endotoxin molecules have a net negative charge. Thus, endotoxin can bind to the positively charged ion exchange resin and be removed from the gelatin-salt solution.

As stated above, Applicants discovered that during endotoxin reduction, a gelatin solution without salt can block/clog the filters of the anion exchange device. Without being bound by a theory, Applicants believe that salt in the gelatin solution can modify the charge on the gelatin molecule to a sufficient level, thereby reducing the adhesion of the gelatin to the anion exchange device. As such, the gelatin-salt solution can pass through the anion exchange device as the filtrate, whereas the endotoxins remain behind.

The anion exchanger can be in the form of a membrane adsorber (e.g., commercially available Sartobind Q from Sartorius Stedim, Mustang E from Pall Life Sciences) or in the form of resin (e.g., commercially available Fractogel EMD TMAE Hicap (M) Resin and Eshmuno Q Resin from Merk Millipore). In addition, the membrane adsorbers are available in a variety of different sizes. For example, the Sartobind Q has several sizes including the 1 mL, 7 mL, 75 mL, 159 mL, 1.2 L, and 5 L bed volume. Selection of the adsorber size can be based on the volume to be filtered, the endotoxin break through point for the solution to be treated, and/or various processing conditions.

Although endotoxin can bind to the positively charged ion exchange resin in the anion exchange device, Applicants discovered that the salt concentration of the gelatin solution can greatly impact the endotoxin removal through the anion exchange device. In order to determine the impact the salt concentration has on endotoxin removal, Applicants prepared a 10% w/w fish gelatin-purified water solution with varying concentrations of sodium chloride and filtered them using a Sartobind Q 1 mL Nano with a 1 mL bed volume. Applicants then measured the endotoxin content as well as the gelatin content in the gelatin-salt solution before and after filtration. The results of the effect of salt concentration on endotoxin removal in the gelatin-salt solution are shown in the following Table 1 and FIG. 4.

TABLE 1

| Pre/Post Filtered Solution | Endotoxin content (EU/g) | Gelatin content (% w/w) |
|---|---|---|
| (10% Gelatin) | 7000 | 10.5; 10.4 |
| Pre Filtration (10% Gelatin + 150 mM NaCl) | 4140 | 10.3; 10.3 |
| Post Filtration (10% Gelatin + 150 mM NaCl) | 191 | 10.1; 10.1 |
| Pre Filtration (10% Gelatin + 250 mM NaCl) | 5760 | 10.0; 10.2 |
| Post Filtration (10% Gelatin + 250 mM NaCl) | 464 | 10.6; 10.7 |
| Pre Filtration (10% Gelatin + 300 mM NaCl) | 4610 | 10.3; 10.6 |
| Post Filtration (10% Gelatin + 300 mM NaCl) | 441 | 10.5; 10.4 |

Figure 4:
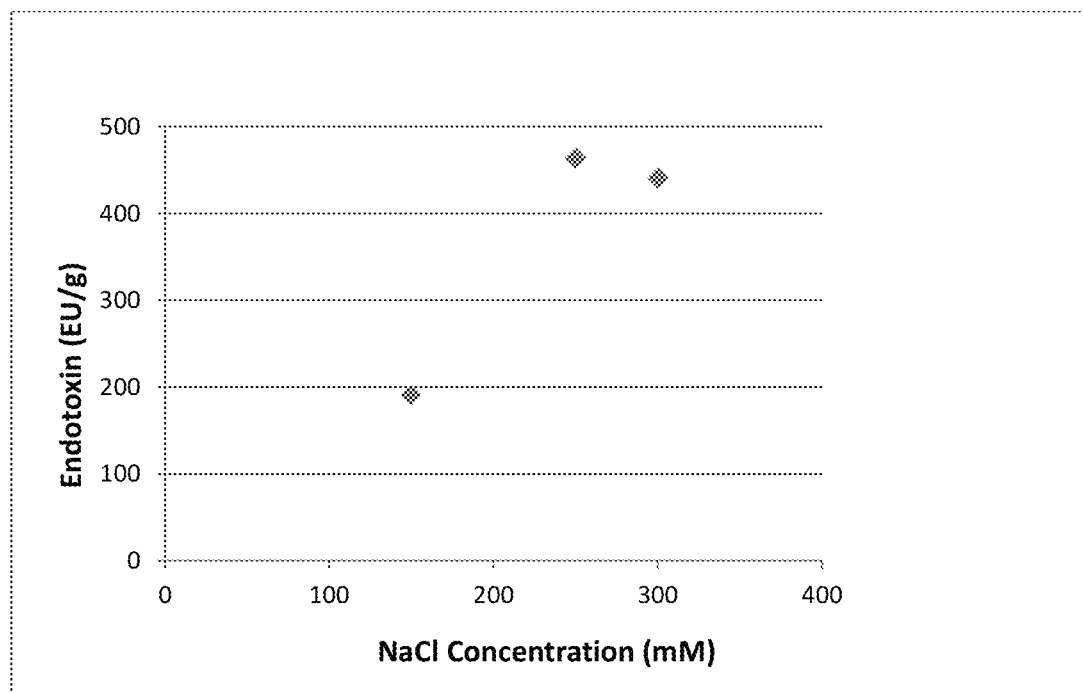
FIG. 4 is a graph illustrating the experimental results of the effect of salt concentration in the gelatin-salt solution on endotoxin removal.

As shown in the above Table 1 and FIG. 4, Applicants discovered that when the salt concentration of the fish gelatin-NaCl solution is around 150 mM, the filter can have the biggest reduction of the endotoxin content in the solution. When the salt concentration is much higher than 150 mM, less endotoxin can be removed. In addition, having a salt concentration much lower than 150 mM may cause the gelatin to clog/block the anion exchange device.

After endotoxin reduction, the conductivity of the filtrate gelatin-salt solution can be measured. In some embodiments, the endotoxin reduction step can reduce the endotoxin content of the gelatin solution by at least about 75%, about 80%, about 85%, about 90%, about 95%, about 98%, or about 99%.

In some embodiments, the endotoxin level in the filtrate gelatin-salt solution can be less than about 3000 EU/g, about 2500 EU/g, about 2000 EU/g, about 1500 EU/g, about 1000 EU/g, about 750 EU/g, about 500 EU/g, about 250 EU/g, about 200 EU/g, about 150 EU/g, or about 100 EU/g. In some embodiments, at least about 85%, about 90%, about 95%, about 98%, or about 99% of the initial gelatin content is recovered after the endotoxin reduction step. This can be assessed by comparing the gelatin concentration pre and post anion exchange filtration.

Desalting the Filtered Gelatin-Salt Solution

Figure 5:
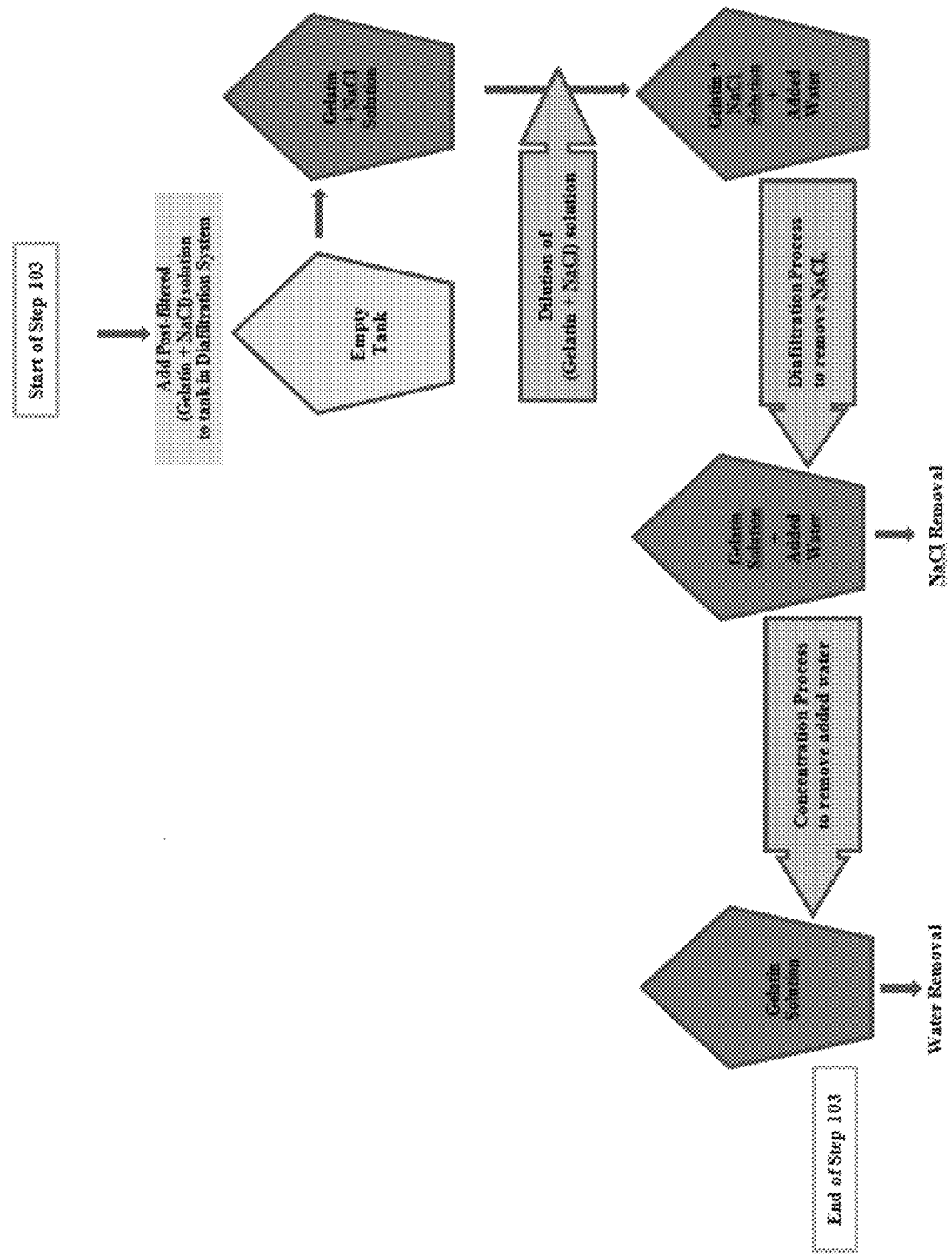
FIG. 5 illustrates a flowchart for a step of desalting the filtered gelatin-salt solution disclosed herein.

After the endotoxin has been reduced in the gelatin-salt solution, the salt that was added in step 101 needs to be removed or reduced in step 103. FIG. 5 illustrates a flowchart for a step of desalting the filtered gelatin-salt solution disclosed herein. One method in which the salt can be removed from the gelatin-salt solution is by diafiltration. Diafiltration is a process that involves removal of salt from a solution based on molecular size using micro-molecule permeable filters. In order to aid the diafiltration, the gelatin-salt solution can be diluted further with water to reduce its viscosity; in particular when the solution has a high gelatin content. The added water can subsequently be removed via a concentration step. In some embodiments, the salt can be removed without dilution of the gelatin-salt solution with water and a subsequent concentration step is therefore not required; for example, for a gelatin-salt solution with lower gelatin content.

The filtered gelatin-salt solution can be inserted into a diafiltration system. Examples of diafiltration systems include, but are not limited to, Sartoflow Advanced crossflow filtration system from Sartorius Stedim, KMPi TFF system from Spectrum Labs (Repligen), or Cogent M1 TFF system from Merck. The weight of the filtered gelatin-salt solution and conductivity can be measured prior to diafiltration.

In some embodiments, the filtrate gelatin-salt solution from the endotoxin reduction step can be diluted by a solvent. In some embodiments, the solvent can be water (including purified water). The ratio of filtrate gelatin-salt solution to solvent can be about 1:1-1:6, about 1:1-1:5, about 1:1-1:4, about 1:1-1:3, about 1:1-1:2, or about 2:1-1:1. In some embodiments, the ratio of filtrate gelatin-salt solution to solvent can depend on the concentration of the gelatin in the filtrate gelatin-salt solution. The gelatin-salt solution and solvent mixture can be stirred and/or heated to ensure sufficient mixing.

The conductivity of the mixture at the start of the diafiltration can be measured. In addition, the conductivity can be continuously monitored and the mixture can be continuously stirred throughout the diafiltration process. Diafiltration can be stopped when the conductivity of the mixture reaches relatively the same or a comparable value of conductivity for the original gelatin solution prior to the addition of salt in step 101. Relatively the same or a comparable value can be when the value is within less than about 25%, about 20%, about 15%, about 10%, about 5%, about 2%, or about 1% the original value.

After salt removal, the diluted gelatin solution can undergo a concentration process. The concentration process can remove the excess solvent added during dilution prior to diafiltration. The concentration process can be accomplished by a concentration system. Examples of concentration systems include, but are not limited to, Sartoflow Advanced crossflow filtration system from Sartorius Stedim, KMPi TFF systems from Spectrum Labs (Repligen), or Cogent M1 TFF system from Merck. Concentration of the diluted gelatin solution can be stopped when the weight of the diluted gelatin solution reaches relatively the same or a comparable weight of the pre-diluted filtrate gelatin-salt solution. Relatively the same or a comparable value can be when the value is within less than about 25%, about 20%, about 15%, about 10%, about 5%, about 2%, or about 1% the original value.

After diafiltration, a low endotoxin gelatin solution remains. In addition, the gelatin concentration or content of this resulting low endotoxin desalted gelatin solution can have relatively the same or similar gelatin concentration/content as the filtered gelatin-salt solution after the endotoxin reduction step. Relatively the same or a comparable value can be when the value is within less than about 25%, about 20%, about 15%, about 10%, about 5%, about 2%, or about 1% the original value. The low endotoxin gelatin solution can have an endotoxin content of less than about 3000 EU/g, about 2500 EU/g, about 2000 EU/g, about 1500 EU/g, about 1000 EU/g, about 750 EU/g, about 500 EU/g, about 250 EU/g, about 200 EU/g, about 150 EU/g, or about 100 EU/g. As such, the endotoxin content after the endotoxin removal step can be maintained during the diafiltration process.

In some embodiments, at least about 85%, about 90%, about 95%, about 98%, or about 99% of the initial gelatin content is recovered after the desalting step. This can be assessed by comparing the gelatin concentration pre and post diafiltration. In some embodiments, at least about 85%, about 90%, about 95%, about 98%, or about 99% of the initial gelatin content is recovered after both the endotoxin reduction and the desalting steps.

In some embodiments, the solvent in the endotoxin reduced gelatin solution can be removed. For example, the endotoxin reduced gelatin solution can be subsequently dried to a solid gelatin with low endotoxin content. This low endotoxin gelatin can be in powder form and can be used as a raw material in a variety of applications including in a pharmaceutical product. In some embodiments, the endotoxin level in the low endotoxin gelatin can be less than about 3000 EU/g, about 2500 EU/g, about 2000 EU/g, about 1500 EU/g, about 1000 EU/g, about 750 EU/g, about 500 EU/g, about 250 EU/g, about 200 EU/g, about 150 EU/g, or about 100 EU/g.

Use in Pharmaceutical Compositions

The low endotoxin gelatin solutions can be used in a variety of pharmaceutical compositions. For example, the low endotoxin gelatin or gelatin solutions produced herein can be used in the dosage forms described in U.S. Pat. Nos. 4,371,516; 4,305,502; and 4,758,598 and GB Patent Nos. 1548022 and 211423, which are hereby incorporated by reference.

In some embodiments, a process of manufacturing a dissolving dosage form for the delivery of a pharmaceutically active ingredient ("API") can include the steps of: (a) dosing a formulation comprising a gelatin into a preformed mold; and (b) freeze drying the formulation to form the dissolving dosage form.

As used herein, "dosed" refers to the deposition of a pre-determined aliquot of solution or suspension. As used herein, "preformed mold" refers to any suitable container or compartment into which an aqueous solution or suspension may be deposited and within which subsequently freeze dried; in certain preferred embodiments of the present disclosure, the preformed mold is a blister pack with one or more blister pockets.

The formulation of step (a) can include a matrix forming agent. The matrix forming agent can be any conventional non-gelling matrix forming agent. Suitable non-gelling matrix forming agents include, without limitation, non-gelling gelatins (including the low endotoxin gelatin prepared according to the process described above), modified starches, pullulan, non-gelling fish gelatin, maltodextrins, low molecular weight dextrans, starch ethers, low to intermediate molecular weight cellulose gums, and combinations thereof. The matrix forming agent can also be any conventional gelling matrix forming agent. Suitable gelling matrix forming agents include, without limitation, gelling gelatin (including the low endotoxin gelatin prepared according to the process described above), carageenan gums, hyaluronic acid, pectins, starches, carboxymethyl cellulose sodium, agar, gellan gum, guar gum, tragacanthan gum, hydroxypropyl cellulose, hydroxy propyl methylcellulose, methylcellulose, carbomer, poloxamer, polyacrylic acid, polyvinyl alcohol, alginates and poly(glycolic acid), and combinations thereof. In some embodiments, the matrix forming agent can be a combination of norm-gelling matrix forming agent and gelling matrix forming agent. One of ordinary skill in the art can readily determine suitable amounts of these matrix forming agents if desired.

The formulation of step (a) is typically in the form of a solution or suspension. Accordingly, a solvent is also present in the formulation. A suitable solvent can be readily chosen by one of ordinary skill in the art once the final composition of the formulation is known, i.e., pharmaceutically active ingredient, excipient, etc. to be present. Preferred solvents include ethanol, isopropanol, other lower alkanols and water, and, more preferably, water.

The formulation of step (a) may also contain an additional pharmaceutically acceptable agent or excipient. Such additional pharmaceutically acceptable agents or excipients include, without limitation, sugars, such as mannitol, dextrose, and lactose, inorganic salts, such as sodium chloride and aluminum silicates, gelatins of mammalian origin, fish gelatin, modified starches, preservatives, antioxidants, surfactants, viscosity enhancers, coloring agents, flavoring agents, pH modifiers, sweeteners, taste-masking agents, and combinations thereof. Suitable coloring agents include red, black and yellow iron oxides and FD & C dyes such as FD & C Blue No. 2 and FD & C Red No. 40, and combinations thereof. Suitable flavoring agents include mint, raspberry, licorice, orange, lemon, grapefruit, caramel, vanilla, cherry and grape flavors and combinations of these. Suitable pH modifiers include citric acid, tartaric acid, phosphoric acid, hydrochloric acid, maleic acid and sodium hydroxide, and combinations thereof. Suitable sweeteners include aspartame, acesulfame K and thaumatin, and combinations thereof. Suitable taste-masking agents include sodium bicarbonate, ion-exchange resins, cyclodextrin inclusion compounds, adsorbates or microencapsulated actives, and combinations thereof. One of ordinary skill in the art can readily determine suitable amounts of these various additional excipients if desired. Mannitol, which is an organic compound with the formula $(C_6H_8(OH)_6)$ and is known generally to those in the art, is a preferred additional pharmaceutically acceptable agent.

The formulation of step (a) may also contain a pharmaceutically active ingredient. As used herein, "pharmaceutically active ingredient" refers to a drug product that may be used in the diagnosis, cure, mitigation, treatment or prevention of disease. Any pharmaceutically active ingredient may be used for purposes of the present disclosure. Of course, one of ordinary skill in the art will readily understand that certain pharmaceutically active ingredients are more suitable for use with the non-gelling matrix forming agent of the formulation of step (a) than with, for example, the gelling matrix forming agent of step (b). Suitable pharmaceutically active ingredients include, without limitation: analgesics and anti-inflammatory agents, antacids, anthelmintics, anti-arrhythnic agents, anti-bacterial agents, anti-coagulants, anti-depressants, anti-diabetics, anti-diarrheals, anti-epileptics, anti-fungal agents, anti-gout agents, antihypertensive agents, anti-malarials, anti-migraine agents, anti-muscarinic agents, anti-neoplastic agents and immunosuppressants, anti-protazoal agents, antirheumatics, anti-thyroid agents, antivirals, anxiolytics, sedatives, hypnotics and neuroleptics, beta-blockers, cardiac inotropic agents, corticosteroids, cough suppressants, cytotoxics, decongestants, diuretics, enzymes, anti-parkinsonian agents, gastro-intestinal agents, histamine receptor antagonists, lipid regulating agents, local anesthetics, neuromuscular agents, nitrates and anti-anginal agents, nutritional agents, opioid analgesics, oral vaccines, proteins, peptides and recombinant drugs, sex hormones and contraceptives, spermicides, and stimulants; and combinations thereof. A list of specific examples of these active ingredients may be found in U.S. Pat. No. 6,709,669, which is incorporated herein by reference. When present, the pharmaceutically active ingredient is present in the formulation of step (a) in an amount that is necessary to exhibit the required physiological effect as established by clinical studies. One of ordinary skill in the art can readily determine an appropriate amount of active ingredient to include in the dosage form made according to the present disclosure.

The formulation of step (a) can be made by any conventional method, which is herein incorporated by reference. Most typically, the matrix forming agent, solvent and optional ingredients may be mixed together at a given temperature to form a solution. In some embodiments, the matrix forming agent and the solvent can be the low endotoxin gelatin solution prepared according to the process described above. Any optional ingredients can be mixed with the gelatin solution. The solution may then be cooled at which point the active ingredient may be added.

Likewise the dosing of step (a) can be accomplished by any known method or apparatus including sequential dosing described in WO 2011/115969.

In step (b), the formulations dosed in step (a) is freeze dried to form the dissolving dosage form. Typically, the dosed formulations in the preformed molds are frozen by any means known in the art, for example by passing them through a liquid nitrogen tunnel, preferably for about one to about ten minutes. One of ordinary skill in the art would readily understand the speed with which to pass them through the tunnel. The dosed formulations in the preformed molds can then be freeze dried under low pressure (i.e., vacuum).

The dosage forms of the present disclosure are dissolving dosage forms and accordingly have the distinct advantage of a faster disintegrating time. The route of administration may be oral, vaginal or nasal, though preferably oral. Once placed in the oral cavity and in contact with saliva, a dosage form can disintegrate within about 1 to about 180 seconds, about 1 to about 120 seconds, about 1 to about 60 seconds, preferably within about 1 to about 30 seconds, more preferably within about 1 to about 10 seconds and most preferably in less than about 5 seconds.

In some embodiments, the dosage forms can have less than about 200 EU/dosage form, less than about 150 EU/dosage form; less than about 125 EU/dosage form; less than about 100 EU/dosage form; less than about 90 EU/dosage form; less than about 75 EU/dosage form; or less than about 50 EU/dosage form.

EXAMPLES

As an initial matter, all vessels and laboratories items used for the manufacture of the gelatin-salt solution should be cleaned and sanitized as required to minimize bioburden and/or introduction of additional endotoxin.

Example 1

An amount of fish gelatin containing approximately 7000 EU/g of gelatin was added to an amount of purified water and fully dissolved (with the aid of heating to approximately 60° C. to facilitate the gelatin to dissolve) to give rise to a 10% w/w fish gelatin solution. The solution was then cooled to room temperature and a reference sample was taken for conductivity measurement. Next, an amount of sodium chloride ("NaCl") was added to the gelatin solution to give a NaCl concentration of 150 mM in the gelatin-NaCl solution. The conductivity of the gelatin-NaCl solution was then measured.

Before the endotoxin removal, the anion exchange device (Sartobind Q Single Sep mini—7 mL filter) was prepped. Pre-use preparation of the anion exchange device and associated tubing was carried out as per the pre-treatment procedure. A 1M sodium hydroxide ("NaOH") solution was used to clean and sanitize the system followed by flushing the system with a 1M NaCl solution to remove the NaOH solution. The adsorber was primed with the gelatin-NaCl solution to remove the 1M NaCl solution used for pre-use preparation. Using a peristaltic pump, gelatin-NaCl solution was then loaded and driven through the Sartobind Q Single Sep mini—7 mL filter. The pump was set to maintain a constant pressure to drive the solution through the adsorber with a minimum build-up of back pressure. The filtered gelatin-NaCl solution was collected in a clean container and the conductivity of this filtered solution was measured.

Figure 6:
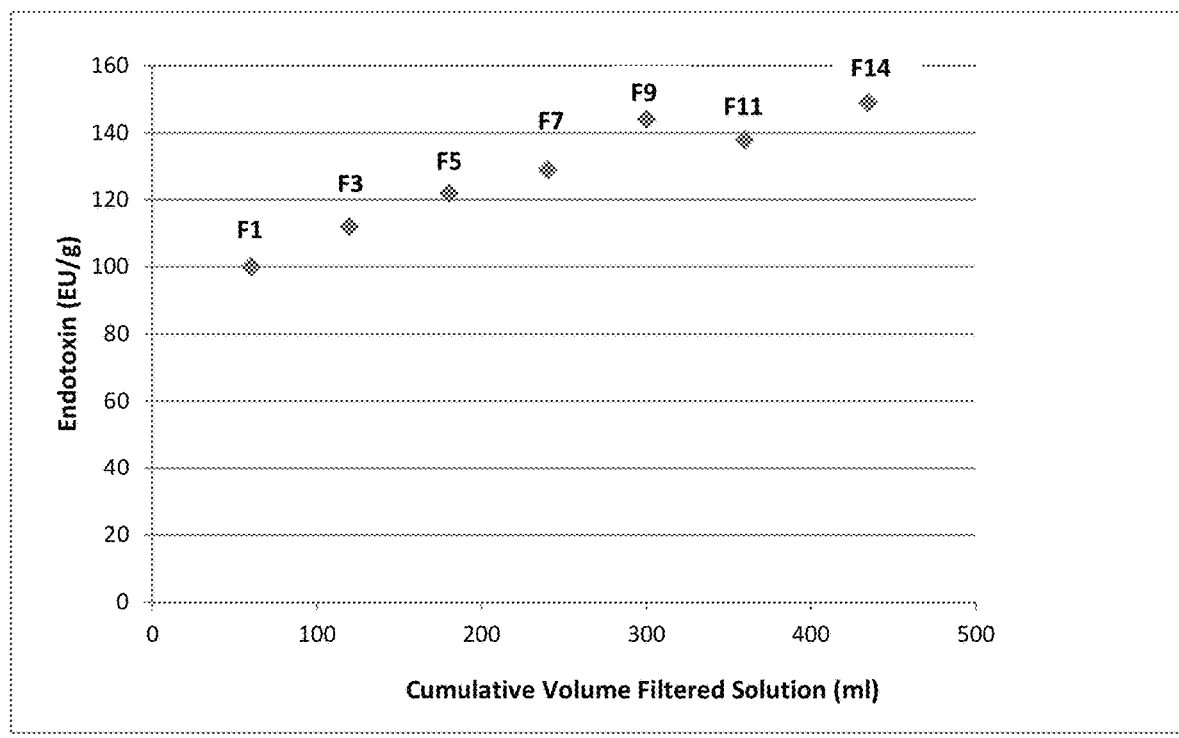
FIG. 6 is a plot of endotoxin in sample fractions against cumulative volume of gelatin-salt solution filtered in Example 1.

Approximately 435 g of the gelatin-NaCl solution (in 30 g fractions) was filtered through a Sartobind Q Single Sep mini—7 mL filter. The binding capacity and break through point of the filter with respect to endotoxin was assessed by collecting fractions of the filtrate at regular intervals and assessed for the endotoxin content and the gelatin assay content. The results are summarized in the following Table 2 and FIG. 6.

TABLE 2

| | Cumulative Weight of filtered Gelatin Solution (g) | Endotoxin content (EU/g) | Gelatin Assay content (% w/w) |
|---|---|---|---|
| Step 101: Gelatin Solution Preparation | | | |
| 10% gelatin solution | 0 | Not tested | Not tested |
| 10% gelatin solution with 150 mM NaCl | 0 | 6440 | 10.3; 10.3 |
| Step 102: Endotoxin Reduction | | | |
| Priming | 30 | N/A | N/A |
| Filtered Fraction 1 | 60 | <100 | 10/5; 10.2 |
| Filtered Fraction 2 | 90 | Not tested | Not tested |
| Filtered Fraction 3 | 120 | 112 | 10.6; 10.4 |
| Filtered Fraction 4 | 150 | Not tested | Not tested |
| Filtered Fraction 5 | 180 | 122 | 10.4; 10.5 |
| Filtered Fraction 6 | 210 | Not tested | Not tested |
| Filtered Fraction 7 | 240 | 129 | 10.4; 10.4 |
| Filtered Fraction 8 | 270 | Not tested | Not tested |
| Filtered Fraction 9 | 300 | 144 | 10.3; 10.5 |

TABLE 2-continued

| | Cumulative Weight of filtered Gelatin Solution (g) | Endotoxin content (EU/g) | Gelatin Assay content (% w/w) |
|---|---|---|---|
| Filtered Fraction 10 | 330 | Not tested | Not tested |
| Filtered Fraction 11 | 360 | 138 | 10.7; 10.5 |
| Filtered Fraction 12 | 390 | Not tested | Not tested |
| Filtered Fraction 13 | 420 | Not tested | Not tested |
| Filtered Fraction 14 | 435 | 149 | 10.6; 10.6 |

Table 2 demonstrates that the endotoxin in the gelatin was reduced by the Sartobind Q filter device. The data also shows a plateauing of the endotoxin level after 300 g (after fraction 9) of the solution has been filtered, with the device eventually blocked at fraction 14, when only 15 mL was collected due to blockage of the adsorber. This indicates that an equilibrium condition was reached in the adsorber tested when approximately 300 g of the gelatin-salt solution had passed through. Instead of a breakthrough of endotoxin, continuing accumulation of the endotoxin on the filter device led to eventual blockage of the device.

UV spectroscopy assay was also performed in the pre-filtered and post-filtered gelatin-salt solution sample and gave the same assay content, confirming that no gelatin was removed during the filtration process.

Example 2

An amount of fish gelatin containing approximately 14,600 EU/g of gelatin was added to an amount of purified water and fully dissolved (with the aid of heating to approximately 60° C. to facilitate the gelatin to dissolve) to give rise to a 12% w/w fish gelatin solution. The solution was then cooled to room temperature and a reference sample was taken for conductivity measurement. Next, an amount of sodium chloride ("NaCl") was added to the gelatin solution to give an NaCl concentration of 150 mM in the gelatin-NaCl solution. The conductivity of the gelatin-NaCl solution was then measured.

Before the endotoxin removal, the anion exchange device (Sartobind Q 75 mL capsule) was prepped. Pre-use preparation of the anion exchange device and associated tubing was carried out as per the pre-treatment procedure. A 1M sodium hydroxide ("NaOH") solution was used to clean and sanitize the system followed by flushing the system with a 1M NaCl solution to remove the NaOH solution. The adsorber was primed with the gelatin-NaCl solution to remove the 1M NaCl solution used for pre-use preparation. Using a peristaltic pump, gelatin-NaCl solution was then loaded and driven through the Sartobind Q 75 mL. The pump was set to maintain a constant pressure to drive the solution through the adsorber with a minimum build-up of back pressure. The filtered gelatin-NaCl solution was collected in a clean container and the conductivity of this filtered solution was measured.

Figure 7:
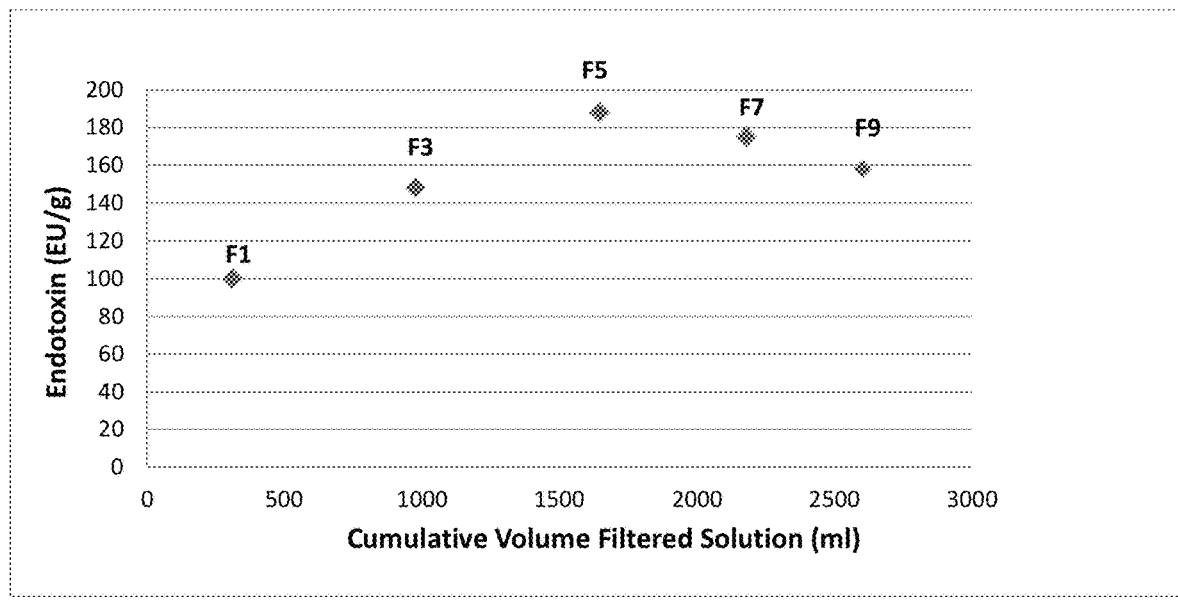
FIG. 7 is a plot of endotoxin in sample fractions against cumulative volume of gelatin-salt solution filtered in Example 2.

Approximately 3000 g of the gelatin-NaCl solution was filtered through a Sartobind Q 75 mL filter. The binding capacity and break through point of the filter with respect to endotoxin was assessed by collecting fractions of the filtrate at regular intervals and assessed for the endotoxin content and the gelatin assay content. The results are summarized in the following Table 3 and FIG. 7.

TABLE 3

| | Cumulative Weight of Filtered Gelatin Solution (g) | Conductivity (mScm) | Endotoxin content (EU/g of gelatin) | Gelatin Assay content (% w/w) |
|---|---|---|---|---|
| Step 101: Gelatin Solution Preparation | | | | |
| 12% gelatin solution | 0 | (0.8-0.9)* | 14600 | Not tested |
| 12% gelatin solution with 150 mM NaCl Pre filtration | 0 | Not tested | 13600 | 12.4; 12.2 |
| Step 102: Endotoxin Reduction | | | | |
| Priming | 224 | — | — | — |
| Filtered Before Fraction1 | 312 | — | — | — |
| Filtered Fraction 1* | 335 | — | <100 | 12.1; 12.3 |
| Filtered Before Fraction 2 | 588 | — | — | — |
| Filtered Fraction 2* | 611 | — | Not tested | Not tested |
| Filtered Before Fraction 3 | 937 | — | — | — |
| Filtered Fraction 3* | 960 | — | 148 | 12.4; 12.6 |
| Filtered Before Fraction 4 | 1230 | — | — | — |
| Filtered Fraction 4* | 1253 | — | Not tested | Not tested |
| Filtered Before Fraction 5 | 1623 | — | — | — |
| Filtered Fraction 5* | 1648 | — | 188 | 12.2; 12.2 |
| Filtered Before Fraction 6 | 1905 | — | — | — |
| Filtered Fraction 6* | 1927 | — | Not tested | Not tested |
| Filtered Before Fraction 7 | 2184 | — | — | — |
| Filtered Fraction 7* | 2203 | — | 175 | 12.2; 12.3 |
| Filtered Before Fraction 8 | 2419 | — | — | — |
| Filtered Fraction 8* | 2437 | — | Not tested | Not tested |
| Filtered Before Fraction 9 | 2604 | — | — | — |
| Filtered Fraction 9* | 2617 | — | 158 | 12.3; 12.3 |
| Total Filter Fraction collected (Fraction 1-9) | 188 | — | — | — |
| Total Filtered gelatin solution collected (excluding fractions 1-9) | 2429 | 13.4 | 119; <100 | Not tested |

*Sample fractions collected were approximately 20 g each.

Table 3 demonstrates that the Sartobind Q 75 mL has the ability to reduce the endotoxin level in a batch of gelatin with an initial endotoxin level equivalent to 14,600 EU/g of gelatin to less than 200 EU/g of gelatin. As such, approximately 2.5 kg of a 12% w/w gelatin-salt solution can be filtered using the 75 mL capsule, with the endotoxin level starting to plateau after approximately 1.6 kg (after fraction 5) of the 12% w/w/ gelatin-salt solution has been filtered suggesting an equilibrium position was reached. No break through point was observed.

The gelatin assay of the solution showed no appreciable change in assay content between the pre and post filtered gelatin solutions, confirming no loss of gelatin to the anion exchange membrane adsorber.

Example 3

An amount of fish gelatin containing approximately 14,600 EU/g of gelatin was added to an amount of purified water and fully dissolved (with the aid of heating to approximately 60° C. to facilitate the gelatin to dissolve) to give rise to a 12% w/w fish gelatin solution. The solution was then cooled to room temperature and a reference sample was taken for conductivity measurement. Next, an amount of sodium chloride ("NaCl") was added to the gelatin solution to give an NaCl concentration of 150 mM in the gelatin-NaCl solution. The conductivity of the gelatin-NaCl solution was then measured.

Before the endotoxin removal, the anion exchange device (Sartobind Q 75 mL capsule) was prepped. Pre-use preparation of the anion exchange device and associated tubing was carried out as per the pre-treatment procedure. A 1M sodium hydroxide ("NaOH") solution was used to clean and sanitize the system followed by flushing the system with a 1M NaCl solution to remove the NaOH solution. The adsorber was primed with the gelatin-NaCl solution to remove the 1M NaCl solution used for pre-use preparation. Using a peristaltic pump, gelatin-NaCl solution was then loaded and driven through the Sartobind Q 75 mL. The pump was set to maintain a constant pressure to drive the solution through the adsorber with a minimum build-up of back pressure. The filtered gelatin-NaCl solution was collected in a clean container and the conductivity of this filtered solution was measured.

Approximately 5000 g of the gelatin-NaCl solution was filtered through a Sartobind Q 75 mL filter. Fifteen (15) of the filtered fractions, each approximately 20 g were sampled for testing. Between the successive fractions, approximately 300 g of the gelatin solution was filtered through.

The first 2000 g of filtered gelatin-salt solution was transferred to the diafiltration system (Sartorius Sartoflow Advanced) to remove the salt by diafiltration and concentration processes. The diafiltration system was set as per operational instruction. Pre-use preparation of the diafiltration system was then carried out to clean and sanitize the system as per operational instructions. A 1M NaOH solution was used to clean and sanitize the system followed by flushing the system with purified water to remove the NaOH solution. A pre-use clean water flux was performed on the diafiltration system to check that the cross-flow filter (cassette) is clean and performing to requirements. This was followed by optimization of the set up parameters (pressure and flow rate) prior to diafiltration commencement.

The filtered gelatin-salt solution was loaded into the tank of the diafiltration system. The weight of solution that was loaded into the tank was recorded and conductivity of the loaded solution was measured using a conductivity probe. The loaded filtered gelatin-salt solution was diluted with purified water (having a ratio of filtered gelatin-salt solution: water of 2:1 or 1:1 or 1:2 or 1:3 or 1:4 depending on the concentration of the gelatin). The mixture was stirred to ensure that the mixture was well mixed.

The diafiltration system was then set for diafiltration under constant volume. Once the system was stabilized, diafiltration to remove the salt was initiated. The conductivity of the solution at the start of the diafiltration was recorded. The conductivity was monitored and the mixture was constantly stirred throughout the diafiltration process. The diafiltration process was stopped when the conductivity reached the same value of the conductivity for the reference gelatin solution sample.

The diafiltration system was then set to concentrate the diluted desalted gelatin solution by removing the excess water added for dilution until the weight of the desalted gelatin solution was the same of the pre-diluted filtered gelatin-salt solution. Upon completion, the diafiltration system was cleaned and a post-use clean water flux was then carried out to check that the cross-flow filter (cassette) was cleaned.

Figure 8:
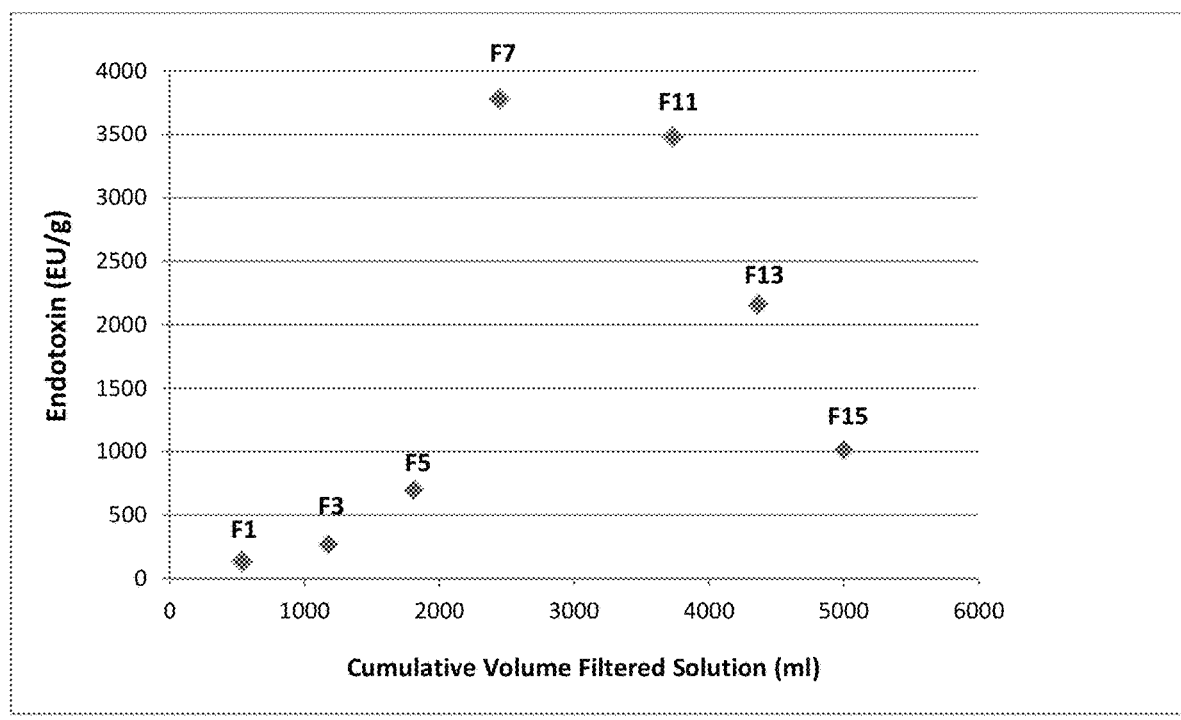
FIG. 8 is a plot of endotoxin in sample fractions against cumulative volume of gelatin-salt solution filtered in Example 3.

Filtration of the remaining gelatin-salt solution (about 3000 g) was continued until the end. The binding capacity and break through point of the filter with respect to endotoxin was assessed by collecting fractions of the filtrate at regular intervals and assessed for the endotoxin content and the gelatin assay content. The results are summarized in the following Table 4 and FIG. 8.

TABLE 4

|  | Cumulative weight of filtered Gelatin Solution (g) | Conductivity (mScm) | Endotoxin content (EU/g of gelatin) | Gelatin Assay content (%) |
| --- | --- | --- | --- | --- |
| Step 101: Gelatin Solution Preparation | | | | |
| 12% gelatin solution | 0 | (~−0.9)* | 14,600 | |
| 12% gelatin solution with 150 mM NaCl | 0 | 13.2 | 14000 | 12.4; 12.6 |
| Step 202: Endotoxin reduction | | | | |
| Priming | (224) | — | N/A | N/A |
| Filtered before Fraction 1 | 524 | — | — | — |
| Filtered Fraction 1* | 540 | | 134 | 12.6; 12.6 |
| Filtered before Fraction 2 | 840 | — | — | — |
| Filtered Fraction 2* | 857 | | Not tested | Not tested |
| Filtered before Fraction 3 | 1157 | — | — | — |
| Filtered Fraction 3* | 1177 | | 269 | Not tested |
| Filtered before Fraction 4 | 1476 | — | — | — |
| Filtered Fraction 4* | 1494 | | Not tested | Not tested |
| Filtered before Fraction 5 | 1794 | — | — | — |
| Filtered Fraction 5* | 1810 | | 697 | 12.4; 12.4 |
| Filtered before Fraction 6 | 2110 | — | — | — |
| Filtered Fraction 6* | 2127 | | Not tested | Not tested |
| *Filtered gelatin solution collected was transferred for diafiltration (~cumulative volume 2 L) | | | | |
| Filtered before Fraction 7 | 2427 | — | — | — |
| Filtered Fraction 7 | 2449 | — | 3780 | Not tested |
| Filtered before Fraction 8 | 2748 | — | — | — |
| Filtered Fraction 8 | 2771 | — | Not tested | Not tested |
| Filtered before Fraction 9 | 3071 | — | — | — |
| Filtered Fraction 9 | 3092 | — | Not tested | 12.3, 12.5 |
| Filtered before Fraction 10 | 3392 | — | — | — |
| Filtered Fraction 10 | 3412 | — | Not tested | Not tested |
| Filtered before Fraction 11 | 3712 | — | — | — |
| Filtered Fraction 11 | 3732 | — | 3480 | Not tested |
| Filtered before Fraction 12 | 4032 | — | — | — |
| Filtered Fraction 12 | 4051 | — | Not tested | Not tested |
| Filtered before Fraction 13 | 4351 | — | — | — |
| Filtered Fraction 13 | 4366 | — | 2160 | 12.9; 12.4 |
| Filtered before Fraction 14 | 4666 | — | — | — |
| Filtered Fraction 14 | 4690 | — | Not tested | Not tested |
| Filtered before Fraction 15 | 4990 | — | — | — |
| Filtered Fraction 15 | 5002 | — | 1010 | 12.3; 12.4 |
| Step 103: Removal of NaCl | | | | |
| *Filtered gelatin collected/Pre Diafiltration | N/A | — | Not tested | Not tested |
| *Filtered gelatin solution collected/Post Diafiltration | N/A | 1.2 | 405 | 11.6; 11.4 |

*Conductivity determined as separate reference sample.

Table 4 demonstrates that the Sartobind Q 75 mL has the ability to reduce the endotoxin level in a batch of gelatin with an endotoxin level equivalent to 14/600 EU/gram of gelatin to less than 1000 EU/gram of gelatin for approximately the first 2 kg of a 12% w/w/gelatin-salt solution. The endotoxin level was maintained when this material was processed through the diafiltration system. For the next 3 kg of the gelatin-salt solution that was filtered, the endotoxin level continued to increase followed by a decrease. This suggested a breakthrough of endotoxin after a volume of 2 kilograms being filtered using the Sartobind Q 75 mL.

With respect to the gelatin content, the endotoxin reduced filtered samples did not show a substantial difference in gelatin assay when compared to the pre-filtered samples. This confirmed (as with the previous Examples) that the gelatin was not binding to the anion exchange adsorber membrane during filtration. For the post diafiltration sample, the sample showed comparable gelatin assay content. Furthermore, the conductivity measurements of the desalted sample showed comparable conductivity value to that of the pre-salted sample, confirming that the de-salting process was a success.

Example 4

For example 4, a batch of freeze-dried tablets were manufactured with endotoxin reduced fish gelatin aqueous solution using the three steps described in FIGS. 2, 3, and 5. The purified water used for example 4 had an endotoxin level of less than 0.1 EU/ml.

A 3 kg fish gelatin-sodium chloride aqueous solution containing 9% w/w fish gelatin and 150 mM NaCl was prepared as described in FIG. 2 and the accompanying paragraphs. The fish gelatin was added to the purified water and fully dissolved (with the aid of heating to approximately 60° C.) to give rise to a fish gelatin solution. The solution was cooled to room temperature and NaCl was added to the fish gelatin solution. The endotoxin level of the resulting gelatin-salt solution was measured and reported to be 1,100 EU/g.

To reduce the endotoxin in the gelatin-salt solution, the solution was filtered through the anion exchange device (Sartobind Q 75 mL capsule) as described with respect to FIG. 3 and the accompanying paragraphs. Prior to filtration, the Sartobind Q capsule and associated tubing were cleaned and sanitized by pumping using 1M sodium hydroxide solution through the system using a peristaltic pump. This was followed by pumping purified water through the system to remove the sodium hydroxide solution. The system was then primed by pumping 1M NaCl solution through the system, followed by a portion of the gelatin-salt solution to remove the NaCl solution. This portion of the gelatin-salt solution was discarded.

The remaining portion of the gelatin-salt solution was filtered through the Sartobind Q filter to reduce its endotoxin content. The filtrate gelatin-salt solution collected was approximately 2.3 kg. The filtrate gelatin-salt solution was then transferred to a diafiltration system (Sartorius Sartoflow Advanced) to remove the salt by diafiltration and concentration processes described in FIG. 5 and the accompanying paragraphs.

Prior to starting the desalting/concentration process, the diafiltration system was cleaned and sanitized using 1M NaOH solution followed by flushing with purified water. A pre-use clean water flux was also performed on the system. The system was then set up for optimal pressure and flow rate using a 10 kDa cross flow filter (cassette).

The diafiltration system was then set for diafiltration under constant volume. The conductivity of the solution was monitored and the diafiltration process was stopped when the conductivity reached the target value which was less than 0.5 mScm$^{-1}$ in this example. The diafiltration system was then set to concentrate the filtered desalted gelatin solution to a target gelatin concentration of 12% w/w (range of 10-14%). On completion, the resulting gelatin solution (filtered-desalted/concentrated) was measured of gelatin and endotoxin content. The resultant solution had a gelatin content of 11% w/w and an endotoxin level of 83 EU/g. Approximately 1.8 kg of the resultant gelatin solution was collected.

The following Table 5 summarizes the manufacturing of freeze-dried tablets with the low endotoxin gelatin of Example 5.

TABLE 5

| Ingredient | % w/w | Amount in mg for a 500 mg aliquot for dosing | Amount in mg post freeze drying |
| --- | --- | --- | --- |
| Buffer solution (to simulate a liquid vaccine formulation) | 25% | 125 mg | ~2.6 mg ** |
| Low endotoxin fish gelatin (in a target 12% w/w fish gelatin solution) | 50% | 250 mg (contains 30 mg fish gelatin) | 30 mg ** |
| Mannitol | 8% | 40 mg | 40 mg |
| Trehalose | 0.75% | 3.75 mg | 3.74 mg |
| pH modifier | qs pH range 6.5-7.8 | ~1.3 mg | ~0.04 mg ** |
| Water (for preparing the aqueous matrix mixture | qs 100% | ~73.5 mg | Water removed |

** after water removed during freeze drying

In this example, a simulated vaccine formulation mixture of 1 kg was prepared for the manufacture of freeze dried tablets. The formulation mix contained 50% w/w of the endotoxin reduced filtered fish gelatin solution (i.e. 0.5 kg of the filtered fish gelatin solution prepared above was used in the manufacture). The formulation was prepared by adding and dissolving the mannitol and trehalose in the filtered fish gelatin solution at temperature between 13-17° C. The pH was adjusted to a target pH of 7.4 using a pH modifier (e.g. 3% NaOH solution). Then the simulated liquid vaccine formulation (in this case a buffer solution) was added and the pH was checked that it is still within the pH range set. Next, water was added to make it up to batch size.

The formulation was dosed by weight (wet dose) into the pockets of preformed blister packs. In this case, an aliquot of 500 mg was dosed in each pocket on the preformed blister. Once dosed, the blister packs were passed through a liquid nitrogen freezing tunnel where the water in the mixture was frozen within the blister pockets. On exiting the freeze tunnel, the product was stored frozen in refrigerated cabinets prior to freeze-drying. The required frozen hold time (also referred to annealing time) was applied to the frozen tablets to anneal the tablets. In this case, a 6 hour frozen hold time was used. The frozen tablets were then loaded onto the shelves of a freeze-dryer where the ice crystals were removed from the frozen tablets by sublimation at low pressure. The resulting freeze-dried tablets had a very high porosity which allowed rapid disintegration. This is characterised by an in-house dispersion time test (wetting and dissociation times). Samples of five resulting freeze-dried tablets were tested and these were found to be typically less than 10 seconds. The results are summarised in Table 6. In some embodiments, a dispersion time of up to 60 seconds is also considered acceptable for product when a slower tablet dispersion/disintegration profile is required. The resulting freeze-dried tablets were also assessed for endotoxin content. This was found to be on average less than 75 EU per tablet.

TABLE 6

| Tablet wetting time | | Tablet dissociation time | |
|---|---|---|---|
| Range (n = 5) Seconds | Mean Time (n = 5) Seconds | Range (n = 5) Seconds | Mean Time (n = 5) Seconds |
| <2-<4 | <3 | <5-<7 | <6 |

Methods of Measurement

Conductivity measurement: The conductivity of a solution is measured using a conductivity meter. The conductivity meter measures the amount of charged particles or ions in the solution. The ions responsible for the conductivity come from electrolytes dissolved in water. Salts (like Sodium Chloride), acid and bases are all electrolytes. The conductivity value is proportional to the concentration of the electrolytes. The conductivity probe is calibrated using a conductivity calibration solution. Then, the conductivity of the solutions is measured. In this disclosure, salt is added to the gelatin solution in step 101 and subsequently removed in step 103 by the desalting process. For completion of the desalting process, the conductivity of the desalted gelatin solution should be comparable to the original gelatin solution (pre-salt addition). Gelatin has some residue ions, so conductivity is measured for the gelatin solution (without salt) to establish the baseline conductivity. This conductivity value is then used to set the diafiltration system. The diafiltration of the solution is progressed until the conductivity reaches this baseline. Once the value is reached, concentration process commenced and the conductivity is maintained.

Endotoxin Content Measurement: The endotoxin content in a solution is determined in accordance with the Pharmacopiea Method "EP2.6.14/USP<81> Bacterial Endotoxins—Method D Chromogenic Kinetic." The test for bacterial endotoxins (BET) is used to detect or quantify endotoxins from gram-negative bacteria using amoebocyte lysate from the horseshoe crab (*Limulus polyphemus* or *Tachypleus tridentatus*). The technique being used for this test is the chromogenic technique, based on the development of color after cleavage of a synthetic peptide-chromogen complex. In practice, a sample of the product is prepared to obtain a 10 mg/mL sample concentration and using a pre-determined dilution (1:1000) tested for endotoxin content using a standard curve for comparison purposes.

Gelatin Assay Content Measurement: UV spectroscopy analysis was used to determine the gelatin content of the solutions disclosed herein. A gelatin assay content calibration curve was established by measuring the UV absorbance of the calibration samples (concentration range between 0.006 and 0.26 mg/ml) at wavelength of 220 nm. For test samples, appropriate amount were weighed into a 100 ml volumetric flask and made up to volume by DI water such that the theoretical concentration of these solution was about 0.05 mg/ml. The UV absorbance of the samples at 220 nm was measured, from which the actual concentration of gelatin in mg/ml was determined. Based on this value, the % gelatin content in the test samples was calculated.

Salt Concentration Measurement: Salt concentration can be determined via conductivity (i.e., using a conductivity meter). A calibration graph can be obtained by measuring the conductivity of a salt solution for a range of salt concentrations. Gelatin can have some residue electrolytes; hence the baseline concentration can be ~0.8-1 mScm, for example. When salt is added to the gelatin solution, conductivity can be measured (which will be attributed to the residue electrolytes+the added salt. For example, ~13 mScm). The removal of the added salt can be monitored during diafiltration until it reaches the baseline value again. At this point, it can be assumed that all the salt added is removed.

Salt concentration or conductivity can be measured when the gelatin solution is made; after the salt has been added to the gelatin solution to form the gelatin-salt solution; and throughout the diafiltration process.

Dispersion Characteristics Measurment (in-vitro test): Dispersion Characteristics (in-vitro test): A minimum of 5 tablets are tested. First, a beaker is prepared containing approximately 200 mL of purified water at 20° C.±0.5° C. Each tablet is then removed from the blister package and the tablet is placed base down on the surface of the water. The time is taken for the time each tablet takes to fully wet or dissociate. Wetting is the time taken for the unit to fully wet. The wetting of the tablet can occur in patches, eventually merging together so that the whole unit is wet. The dispersion test is considered complete when the center of the unit is a wetted mass. Thus, the wetting time is taken from when the center of the unit has wetted through as this is the thickest part of the unit. The wetting time is recorded for each of the five tablets. The maximum time for each test is 60 seconds. Time longer than this may be written simply as greater than 60 seconds. Dissociation=the time taken for the unit to break apart. This time can be taken when the unit starts to fall apart at the edges. The dissociation time is recorded for each of the five tablets. The maximum time for each test is 60 seconds. Times longer than this may be written as greater than 60 seconds. Occasionally, the unit will not fully wet or dissociate completely inside of this time limit. At times, the unit may have hard lumps in it; other times it may have not wetted on the surface at all. In addition, the whole unit may be covered in a hard skin. A note of this is made in the description if it happens, citing "hard lumps", or "skin remains", as appropriate. The formation of "hard lumps" and/or "skin" can be an indication of microstructural collapse during freeze-drying. FIGS. 9A-C show a simplified representation of the three possible non-dispersed states, with a side view and a top view of the units as they would appear in the water. The photos in FIGS. 9A-C show some representative units for the same categories. The criterion for the dispersion characteristic test is if the 5 tablets can be fully wetted and/or dissociated into a palpable mass without the presence of hard lumps and skin in 60 seconds or less. In some embodiments, the dosage forms disclosed herein can be fully wetted and/or dissociated into a palpable mass without the presence of hard lumps and/or skin in 60 seconds or less.

Definitions

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

Reference to "about" a value or parameter herein includes (and describes) variations that are directed to that value or parameter per se. For example, description referring to "about X" includes description of "X". In addition, reference to phrases "less than", "greater than", "at most", "at least", "less than or equal to", "greater than or equal to", or other similar phrases followed by a string of values or parameters is meant to apply the phrase to each value or parameter in the string of values or parameters. For example, a statement that a solution has a concentration of at least about 10 mM, about 15 mM, or about 20 mM is meant to mean that the solution has a concentration of at least about 10 mM, at least about 15 mM, or at least about 20 mM.

As used herein, the singular forms "a," "an," and "the" are intended to include the plural forms as well, unless the context clearly indicates otherwise. It is also to be understood that the term "and/or" as used herein refers to and encompasses any and all possible combinations of one or more of the associated listed items. It is further to be understood that the terms "includes, "including," "comprises," and/or "comprising," when used herein, specify the presence of stated features, integers, steps, operations, elements, components, and/or units but do not preclude the presence or addition of one or more other features, integers, steps, operations, elements, components, units, and/or groups thereof.

This application discloses several numerical ranges in the text and figures. The numerical ranges disclosed inherently support any range or value within the disclosed numerical ranges, including the endpoints, even though a precise range limitation is not stated verbatim in the specification because this disclosure can be practiced throughout the disclosed numerical ranges.

The above description is presented to enable a person skilled in the art to make and use the disclosure, and is provided in the context of a particular application and its requirements. Various modifications to the preferred embodiments will be readily apparent to those skilled in the art, and the generic principles defined herein may be applied to other embodiments and applications without departing from the spirit and scope of the disclosure. Thus, this disclosure is not intended to be limited to the embodiments shown, but is to be accorded the widest scope consistent with the principles and features disclosed herein.

The invention claimed is:

1. A method for reducing endotoxin in gelatin, comprising:
    dissolving a salt in a gelatin solution comprising gelatin and a solvent to form a gelatin-salt solution, wherein the endotoxin content of the gelatin is at least 6,000 EU/g and a salt concentration in the gelatin-salt solution is 125-300 mM;
    filtering the gelatin-salt solution through an anion exchange adsorber such that a filtrate gelatin-salt solution has an endotoxin content of less than 2,500 EU/g; and
    desalting the filtrate gelatin-salt solution to form a low endotoxin gelatin solution that has an endotoxin content of less than 2,500 EU/g.

2. The method of claim 1, wherein the salt concentration of the gelatin-salt solution is about 145-155 mM.

3. The method of claim 1, wherein the gelatin solution is a 1-20% w/w gelatin solution.

4. The method of claim 1, wherein the salt is sodium chloride.

5. The method of claim 1, wherein the gelatin is fish gelatin.

6. The method of claim 1, wherein dissolving the salt in the gelatin solution comprises heating the gelatin solution to 50-70° C.

7. The method of claim 1, wherein the solvent is water.

8. The method of claim 1, wherein the endotoxin content of the filtrate gelatin-salt solution and the low endotoxin gelatin solution is less than 1,000 EU/g.

9. The method of claim 1, wherein filtering the gelatin-salt solution through an anion exchange adsorber can reduce the endotoxin content of the solution by at least 95%.

10. The method of claim 1, wherein at least about 85% of the gelatin content is recovered in the filtrate gelatin-salt solution after filtering the gelatin-salt solution through an anion exchange adsorber.

11. The method of claim 1, wherein desalting the filtrate gelatin-salt solution is accomplished by a diafiltration process.

12. The method of claim 11, wherein the diafiltration process comprises diluting the filtrate gelatin-salt solution with a second solvent and filtering the diluted filtrate gelatin-salt solution to form a diluted filtrate gelatin solution.

13. The method of claim 12, wherein the diluted filtrate gelatin-salt solution is filtered until a conductivity of the diluted filtrate gelatin solution is within less than 25% of a conductivity of the gelatin solution.

14. The method of claim 13, wherein the ratio of filtrate gelatin-salt solution to second solvent is 1:1-1:4.

15. The method of claim 14, wherein the second solvent is removed from the diluted filtrate gelatin solution to form the low endotoxin gelatin solution.

16. The method of claim 15, wherein the second solvent is removed from the diluted filtrate gelatin solution until a weight of the diluted filtrate gelatin solution is within less than 5% of a weight of the filtrate gelatin-salt solution.

17. The method of claim 16, wherein the second solvent comprises water.

18. The method of claim 1, further comprising removing the solvent from the low endotoxin gelatin solution to form a low endotoxin gelatin that has an endotoxin content of less than 2,500 EU/g.

* * * * *